United States Patent
Haveri et al.

(10) Patent No.: US 9,572,948 B2
(45) Date of Patent: Feb. 21, 2017

(54) LIQUID SEPARATOR FOR REMOVING A LIQUID FROM A SAMPLE OF A BREATHING GAS AND AIRWAY ADAPTER

(71) Applicant: General Electric Company, Schenectady, NY (US)

(72) Inventors: Heikki Haveri, Huhmari (FI); Kurt Weckstrom, Espoo (FI); Kai Karlsson, Helsinki (FI); Jani Kauppi, Helsinki (FI); Anne Paykkonen, Helsinki (FI); Timo Holopainen, Helsinki (FI); Mikael Alanen, Espoo (FI)

(73) Assignee: General Electric Company, Schenectady, NY (US)

( * ) Notice: Subject to any disclaimer, the term of this patent is extended or adjusted under 35 U.S.C. 154(b) by 502 days.

(21) Appl. No.: 14/135,896

(22) Filed: Dec. 20, 2013

(65) Prior Publication Data

US 2015/0174358 A1    Jun. 25, 2015

(51) Int. Cl.
*A61M 16/14*    (2006.01)
*A61B 5/08*    (2006.01)
(Continued)

(52) U.S. Cl.
CPC ........ *A61M 16/0808* (2013.01); *A61B 5/0876* (2013.01); *A61B 5/097* (2013.01); *A61M 16/0057* (2013.01); *A61M 16/085* (2014.02)

(58) Field of Classification Search
CPC combination set(s) only.
See application file for complete search history.

(56) References Cited

U.S. PATENT DOCUMENTS 4,456,014 A    6/1984  Buck et al.
4,549,553 A   10/1985  Hochberg
(Continued)

FOREIGN PATENT DOCUMENTS

EP    0707827 A1    4/1996
EP    2226116 A2    9/2010
WO  2007020640 A2    2/2007

OTHER PUBLICATIONS

International Search Report and Written Opinion from corresponding PCT application No. PCT/US2014/055787 dated Jan. 5, 2015; 11 pages.

*Primary Examiner* — Michael Kahelin
*Assistant Examiner* — Mitchell E Alter
(74) *Attorney, Agent, or Firm* — Andrus Intellectual Property Law, LLP

(57) ABSTRACT

A liquid separator removing a liquid from a sample of a breathing gas flowing through an airway adapter having a channel surrounded by a wall is disclosed herein. The separator includes a chamber receiving the sample, and a membrane having an outer surface exposed to the gas flow, the membrane at least partially surrounding the chamber, which membrane separates the liquid received by the chamber. The separator also includes a supporting structure for supporting the membrane, and a connector operationally attached to the supporting structure, the connector being connectable to the adapter. The connector comprises a cavity providing a flow path for the sample from the chamber through an opening of the cavity to a sample tube. The membrane branches from a central part of the channel into at least two different branches extending to different directions.

20 Claims, 3 Drawing Sheets

(51) Int. Cl.
  *A61M 16/08* (2006.01)
  *A61B 5/087* (2006.01)
  *A61B 5/097* (2006.01)
  *A61M 16/00* (2006.01)

(56) References Cited

U.S. PATENT DOCUMENTS

| | | | |
|---|---|---|---|
| 4,558,708 | A | 12/1985 | Labuda et al. |
| 4,679,573 | A * | 7/1987 | Parnoff ............... A61B 5/097 600/529 |
| 4,886,528 | A | 12/1989 | Aaltonen et al. |
| 5,657,750 | A * | 8/1997 | Colman ............... A61M 16/105 128/204.13 |
| 6,436,089 | B1 * | 8/2002 | Danielson ......... A61M 39/0247 210/232 |
| 7,121,134 | B2 | 10/2006 | Rich |
| 7,137,390 | B2 | 11/2006 | Fudge et al. |
| 2007/0039374 | A1 | 2/2007 | Borali |
| 2012/0136269 | A1 | 5/2012 | Weckstrom |
| 2013/0116589 | A1 * | 5/2013 | Ophir ............... A61B 5/097 600/543 |

* cited by examiner

Prior art

LIQUID SEPARATOR FOR REMOVING A LIQUID FROM A SAMPLE OF A BREATHING GAS AND AIRWAY ADAPTER

BACKGROUND OF THE INVENTION

This disclosure relates generally to a liquid separator for removing a liquid from a sample of a breathing gas and an airway adapter.

When a patient is mechanically ventilated with a conventional ventilator, an endotracheal tube is placed into a trachea so that it goes through oral or nasal cavity and larynx. The other end of the endotracheal tube is connected to a breathing circuit Y-piece through a luer type connector. If the patient is gas monitored with a sidestream gas analyzer, an airway adapter used for sampling the breathing gas that is analyzed by the gas analyzer is normally connected between connectors of the endotracheal tube and the breathing circuit Y-piece. During an inspiration the fresh breathing gas including higher oxygen ($O_2$) concentration flows into the patients lungs through an inspiratory limb of the breathing circuit Y-piece, the airway adapter, the endotracheal tube and their connectors, then to a trachea, a bronchus, a bronchi, bronchioles and finally reaching an alveoli deep in the lungs, where all the gas exchange actually occurs. Carbon dioxide ($CO_2$) molecules in hemoglobin of a blood flowing in tiny blood vessels around the alveoli are replaced with $O_2$ molecules in the fresh breathing gas through the thin walls of the alveoli. $O_2$ molecules take their place in the hemoglobin, whereas $CO_2$ molecules flow out from the patient within the used expired breathing gas, through the same path as the fresh gas came in during the inspiration. Thus a gas concentration of the breathing gas measured by the gas analyzer is somewhat proportional to the gas concentration in the blood. If anesthetic agents are used they flow in to the patient during inspiration and the content not adsorbed by the patient flows out from the patient during expiration, which can be monitored with a gas analyzer as well.

The conventional patient side part of the breathing circuit, which is also shown in FIG. 1, usually consists of an endotracheal tube 2 connected to a patient 1 and to a sidestream type airway adapter 3 used for sampling the breathing gas for the gas analyzing purposes and a Y-piece 4 that connects the patient side part of the breathing circuit to the ventilator 5 through breathing circuit tubing for inspiratory gas 6 and expiratory gas 7. The gas analyzer 8 is placed further away from the patient close to or into the host device such as the ventilator 5. The breathing gas sample withdrawn from the patient's breathing is sucked by the gas analyzer 8 from the airway adapter 3, through a sampling port 9, which in connection with the breathing gases, through a sampling tube 10 and through a water separation unit 11 into the gas analyzer 8 to be analyzed. The length of the sampling tube 10 may vary from 2 to 6 meters and the inner diameter of the tube may vary from 1.2 to 2 mm. The breathing gas includes close to 100% humidity, which condensates into water in the sampling tube 10. The breathing gas may also include other liquid substances such as blood, mucus etc. that may enter the sampling tube 10. The water separation unit 11 usually comprises a porous membrane or a similar structure that separates the water or liquid substance from the gas flowing in the tube 10, preventing it to enter the sensitive parts inside the analyzer.

The inner diameter and the length of the sampling tube together with the sampling gas flow speed mostly determine the total system response time and the total system rise time of the gas analyzer. The length of the tubing is normally determined by the use environment in the hospital and is between 2 to 6 meters. It would be beneficial to have high sampling gas flow speed to decrease the total system response and rise times, but the tendency is to have the sampling gas flow speed below 200 ml/min or advantageously approximately at 50 ml/min to enable the gas monitoring of small patients whose tidal volumes may be as low as 2 ml. The advantageous choice to decrease the total system response and rise times is to decrease the diameter of the sampling tube. However as the diameter is decreased the condensed water and other liquid substances block the sampling tube easily deteriorating the measurement system rise time and increasing the measurement system response time or even preventing the whole gas analyzing as the sample gas is not allowed to enter the gas analyzer.

Some prior art systems may comprise a cylindrical water separation unit located partially inside the airway adapter breathing flow path and the volume inside the sample gas tube, which is in connection with the airway adapter. Such systems generate high and unwanted flow resistance to the gas flow disturbing the gas exchange in the lungs. Such systems are also position sensitive and easily get blocked by the condensed water and other liquid substances in certain positions.

BRIEF DESCRIPTION OF THE INVENTION

The above-mentioned shortcomings, disadvantages and problems are addressed herein which will be understood by reading and understanding the following specification.

In an embodiment, a liquid separator for removing a liquid from a sample of a breathing gas flowing through an airway adapter having a channel surrounded by a wall, the channel being configured to locate between a patient and a ventilator, includes a chamber configured to receive the gas sample of the breathing gas, and a membrane having an outer surface exposed to the breathing gas flow, the membrane at least partially surrounding the chamber and which membrane is configured to separate the liquid from the gas sample received by the chamber. The liquid separator also includes a supporting structure for supporting the membrane, and a connector operationally attached to the supporting structure and which connector is connectable to the airway adapter, the connector comprising a cavity providing a flow path for the sample gas from the chamber through an opening of the cavity to a sample tube. The membrane is configured to branch from a central part of the channel into at least two different branches, each of the at least two branches extending to different directions to obtain the sample.

In another embodiment, an airway adapter includes a channel surrounded by a wall for a breathing gas flow, the channel being configured to locate between a patient and a ventilator. The airway adapter also includes a first port for delivering breathing gas, and a second port for delivering breathing gas, the second port being in flow communication with the first port through the channel. The airway adapter also includes a liquid separator extending into the channel for removing a liquid from a sample of the breathing gas flowing through the channel, the liquid separator comprising a chamber configured to receive the sample of the breathing gas, and a membrane having an outer surface exposed to the breathing gas flow, the membrane at least partially surrounding the chamber and which membrane is configured to separate the liquid from the gas sample received by the chamber. The liquid separator also includes a supporting structure for supporting the membrane, and a connector operationally attached to the supporting structure, the connector comprising a cavity providing a flow path for the sample gas from the chamber through an opening of the cavity to a sample tube, the connector being operationally connected to the wall. The membrane is configured to branch from a central part of the channel into at least two different branches, each of the at least two branches extending to different directions towards the wall to obtain the sample.

In yet another embodiment, an airway adapter includes a channel surrounded by a wall for a breathing gas flow, the channel being configured to locate between a patient and a ventilator. The airway adapter also includes a first port for delivering breathing gas, and a second port for delivering breathing gas, the second port being in flow communication with the first port through the channel. The airway adapter also includes a liquid separator extending into the channel for removing a liquid from a sample of the breathing gas flowing through the channel, the liquid separator comprising a chamber configured to receive the sample of the breathing gas, and a membrane having an outer surface exposed to the breathing gas flow, the membrane at least partially surrounding the chamber and which membrane is configured to separate the liquid from the gas sample received by the chamber. The liquid separator also includes a supporting structure for supporting the membrane, and a connector operationally attached to the supporting structure, the connector comprising a cavity providing a flow path for the sample gas from the chamber through an opening of the cavity to a sample tube, the connector being operationally connected to the wall. The membrane is configured to branch from a central part of the channel into at least two different branches, each of the at least two branches extending to different directions towards the wall to obtain the sample, and that the branches are configured to restrict the breathing gas flow through the channel providing a signal indicative of the breathing gas flow.

Various other features, objects, and advantages of the invention will be made apparent to those skilled in art from the accompanying drawings and detailed description thereof.

DETAILED DESCRIPTION OF THE INVENTION

Specific embodiments are explained in the following detailed description making a reference to accompanying drawings. These detailed embodiments can naturally be modified and should not limit the scope of the invention as set forth in the claims.

Figure 1:
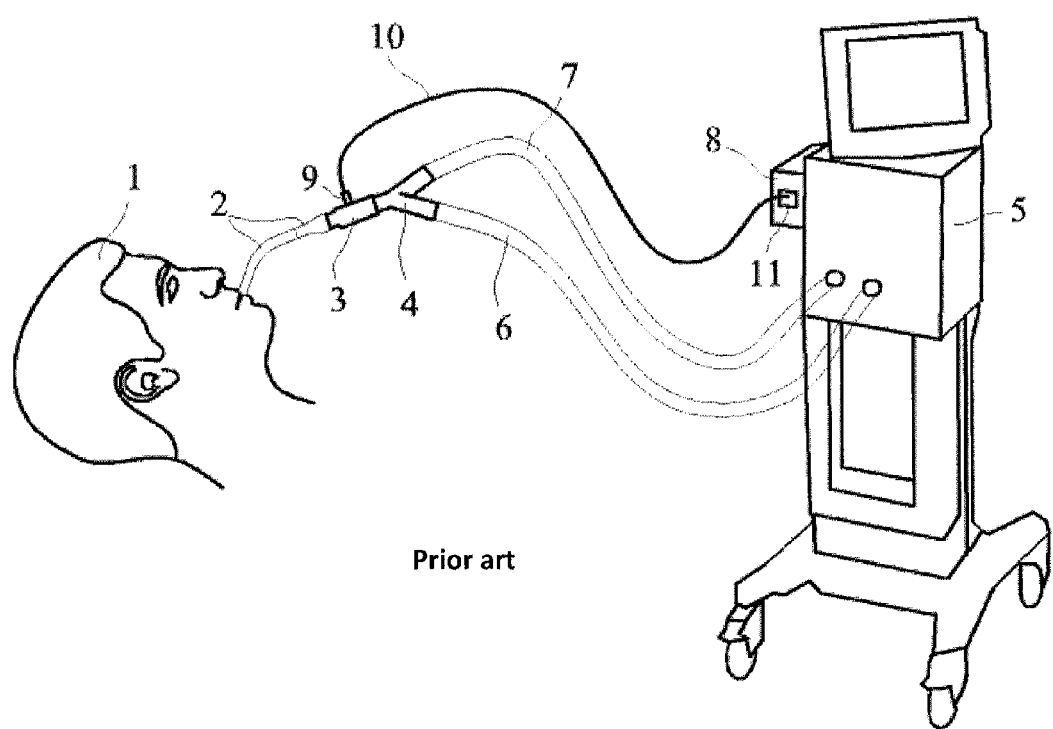
FIG. 1 shows a schematic view of a prior art breathing circuit.
Figure 2:
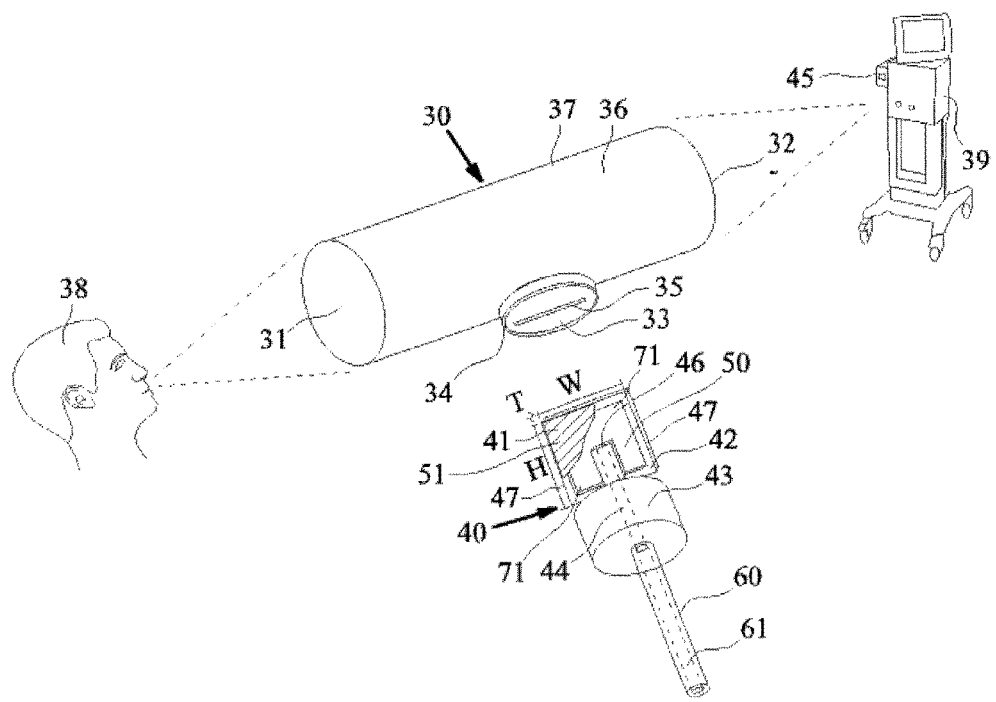
FIG. 2 shows an exploded partial cross-sectional view of an airway adapter with a liquid separator in accordance with an embodiment.
Figure 3:
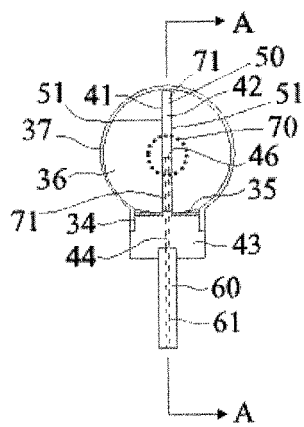
FIG. 3 shows a cross-sectional schematic end view of the airway adapter connected with the liquid separator of FIG. 2.
Figure 4:
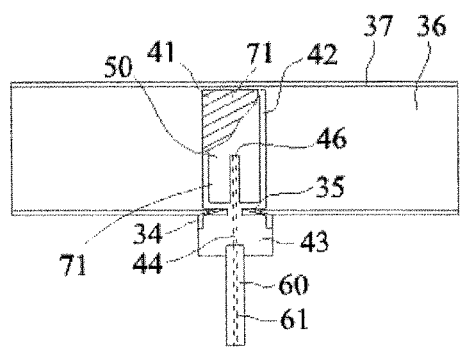
FIG. 4 shows a cross-sectional schematic view of the airway adapter connected with the liquid separator of FIG. 3 taken along lines A-A.

FIG. 2 shows an exploded schematic view of an airway adapter 30 having a first port 31 and a second port 32. The ports may connect typically through an endotracheal tube to a patient 38 and through a breathing circuit Y-piece to a ventilator 39 respectively. The airway adapter 30 comprises a channel 36 which is surrounded by a wall 37, the adapter 30 allowing breathing gases to flow between the first port 31 and the second port 32. Thus the second port is in flow communication with the first port through the channel 36. The adapter may also comprise a liquid separator 40 for removing a liquid, such as water, from a sample of breathing gas flowing through the channel. Furthermore the airway adapter may comprise a third port 33 located between the first port 31 and the second port 32 for the liquid separator 40. The liquid separator 40 can be integrated with the wall 37 or the third port, but as well it can be detachably connected into the third port 33 through an opening 34 to be in connection with the breathing gases flowing between the ports 31 and 32. The liquid separator typically extends into the channel 36 when it is connected to the airway adapter 30 as shown in FIGS. 3 and 4.

The liquid separator 40 comprises a porous membrane 41 having an outer surface 51 exposed to the breathing gas flow enabling the breathing gases to flow through the membrane into the chamber 50, which may be defined by a supporting structure 42, such as a frame, and the membrane 41. The supporting structure is for supporting the membrane 41. The membrane may be attached on both sides of the supporting structure 42, but prevent the liquid, such as water substances to enter through the membrane 41 keeping them outside the chamber 50. The supporting structure 42 may be made of plastic or similar material. The membrane 41, which may be attached on both sides of the supporting structure 42 (only part of the top membrane shown in FIG. 2) by gluing, with ultrasonic welding, with laser welding or similar attaching method to form a double layer construction with clearance between.

The liquid separator 40 further comprises a connector 43 having a fixed or removable connection to a sample tube 60. The connector 43, which may be operationally attached to the supporting structure, comprises a cavity 44 with a predetermined cross sectional area, which is aligned with a tube cavity 61 of the sample tube 60. The cavity 44 opens into the chamber 50 through an opening 46 and the other end of the tube cavity 61 opens into the gas analyzer and is in connection with the gas pump (not shown in FIG. 2). Thus the cavity 44 provides a flow path for the sample gas from the chamber 50 through the opening 46 of the cavity to the sample tube 60 and further to the gas analyzer. In FIG. 2 the supporting structure 42 is rectangular shaped forming a rectangular shape chamber 50, but the supporting structure 42 can be shaped multiform, circular disk or similar as well forming other than rectangular shaped chamber 50. If desired the chamber 50 can be divided into sections.

The connector 43 may be fixedly or removably connected to the opening 33 of port 34 in the airway adapter 30. When the liquid separator 40 is connected to the airway adapter 30 the chamber 50 may locate between the first port 31 and the second port 32 so that the side surfaces 47 of the supporting structure 42 face towards the ports 31 and 32 allowing the breathing gas to flow from the side of the membrane 41. As the gas pump (not shown in Figures) in connection with the sample tube 60 sucks breathing gas through the opening 46, the cavity 44 and the tube cavity 61 it generates an under-pressure into the chamber 50, which causes the breathing gases flowing inside the airway adapter, between the ports 31 and 32, to flow through the membrane 41 into the chamber 50 and through the opening 46 and the cavity 44 and the tube cavity 61 towards the gas analyzer 45. The condensed water or vapor, mucus, blood or similar liquid substances does not penetrate through the membrane 41 into the chamber 50 and the cavity 44 and the tube cavity 61, but stay inside the airway adapter 30 in the channel 36, and outside the chamber 50.

All liquid substances such as water, mucus and blood have inertia as they move within the breathing gas flow. It is advantageous that the side surfaces 47 of the supporting structure 42 face against the first port 31 and the second port 32 whereas the outer surface 51 of membrane 41 is aligned parallel with the breathing gas flowing between the ports 31 and 32 to prevent the excessive liquid substances to collide with the membrane 41 and block the outer surface 51 of membrane 41 preventing the sample gas to flow into the chamber 50. Thus the outer surface 51 of the membrane 41 may extend parallel with a longitudinal axis of the channel 36. It is advantageous to shape the surfaces 47 so that they generate less turbulence into the breathing gas flowing past the surfaces 51 to cause less mixing of gases, especially the boundaries of different gas columns, but also to minimize the liquid substances to collide with the outer surfaces 51 and to resist less the breathing gas flow.

The breathing cycle includes an inspiration and an expiration changing by turns. The volume of inspiration or expiration is called the tidal volume and the frequency the inspiration and the expiration changing by turns is called the respiration rate. The tidal volume and the respiration rate are dependent on the size and the physiology of the patient. In general the tidal volume decreases and the respiration rate increases as the size of the patient decreases.

The size of the chamber 50 needs to be small enough to allow only one gas concentration volume corresponding to the inspiration or the expiration to fill up the volume of the chamber 50 at a time during the respective inspiration or expiration phase to minimize the mixing of different gas concentration columns sucked through the membrane 41 in the chamber 50. The mixing of different concentration gas columns degrade the gas concentration signal rise time that can be seen as rounded transitions in a capnogram. The volume of the chamber 50 may be defined by the thickness of the supporting structure 42, which may be the same as the distance between the membrane 41 on the opposite sides of the chamber 50, and the surface area of the membrane 41. The volume of the chamber 50 can be reduced by decreasing the thickness of the frame 42, which also decreases the undesired flow resistance generated by the areas of the side surfaces 47 of the supporting structure 47. However, the minimum thickness of the supporting structure 42 cannot be smaller than the inner diameter of the opening 46 and the wall thickness of the supporting structure 42 around the opening 46.

To reduce the mixing of gas columns inside the chamber 50 and to minimize the sample gas transit time differences between the different surface areas of the membrane 41 and the opening 46 it is advantageous to locate the opening substantially close into the midpoint in regard to the side surfaces 47 to equalize the distances that the sampled gas needs to travel through the different areas of the membranes 41 into the opening 46.

It is also advantageous to minimize the area of the outer surface 51 to reduce the sample gas transit time differences and the sample gas transit time between the different points across the surfaces of the membrane 41 and the opening 46. On the other hand the membrane 41 must have a certain minimum outer surface area to minimize the pressure difference across the membrane 41, which is inversely proportional to the surface area of the membrane 41 to degrease the work that the gas pump needs to do to generate enough flow to get the gas samples for analyzes. Thus the larger the area of the outer surface of the membrane 41, the smaller the pressure difference across the membranes 41 and the less work the gas pump needs to do. Furthermore the size of the area of the outer surface 51 of the membrane 41 affect to how easy the membrane 41 get blocked due to the collisions with liquid substances. In general the smaller the area of the outer surface 51 of the membrane 41, the easier they get blocked of liquid substances and even harder it gets for the gas pump to suck the gas samples. The height (H) of the supporting structure 42, which may correspond to the length of the side surfaces 47, is advantageous to extend across the inner diameter of the airway adapter 30 to maximize the area of the outer surface 51 of the membrane 41. However it is also advantageous that the side surfaces 47 are not in connection with the inner walls of the airway adapter 30 to prevent the condensed water or other liquid substances floating on the inner walls of the airway adapter to block the membrane. The length of the side surfaces 47 along the direction parallel to the diameter, which is the direction perpendicularly against the direction of breathing gas flow or the longitudinal axis of the channel 36, is advantageous to increase since the boundary of inspiratory and expiratory gases pass the membrane 41 across the whole outer surface area of the membrane 41 simultaneously. This means that the gas samples sucked through across the different areas of the membrane 41 in the direction of the diameter are more synchronous than that in the direction of the breathing gas flow. It is also advantageous direction in transition time difference sense since due to the laminar flow dominating in the airway adapter 30 the breathing gases travel in separate gas concentration columns proportional to inspiration and expiration with a clear boundary.

The fixed connection between the airway adapter 30 and the liquid separator 40 ensure that the there is no leakages in the breathing circuit, but on the other hand the manufacturability of such a complicated combination of parts, as described above, would become more difficult. It is also disadvantageous if there is need for changing the airway adapter, when entire surfaces of the liquid separator 40 has been blocked due to an extensive water or liquid substance such as mucus or blood. When the breathing circuit is opened to replace the airway adapter with a new one the positive end expiratory pressure keeping the sick lungs open is released and the lungs collapse preventing the gas exchange in the alveoli. Thus it is advantageous to have a removable connection between the airway adapter 30 and the liquid separator 40 when the blocked liquid separator is replaced so that there is no need to open the breathing circuit (separating the airway adapter from the endotracheal tube and the breathing circuit Y-piece) and thus loose the positive end expiratory pressure.

The third port 33 may comprise an elastic penetrable membrane 35, which covers the opening 34 preventing the positive end expiratory pressure to escape from the breathing circuit through the opening 34. When the liquid separator 40 is placed into the port 34 the supporting structure 42 and the membrane 41 attached to the supporting structure displace the elastic penetrable membrane 35 attached to the third port 33 covering the opening 34 enabling the supporting structure 42 and the membrane 41 attached to the supporting structure to be placed between the first port 31 and the second port 32. When the liquid separator 40 is removed from the third port 33 the elastic penetrable membrane 35 returns to its closed state preventing the positive end expiratory pressure to escape from the breathing circuit.

Alternatively the connection between the liquid separator 40 and the sample tube 60 can be fixed or removable. The removable connection enables the sample tube 60 to be removed without removing the airway adapter 30 from the breathing circuit and losing the positive end expiratory pressure. However, this does not help the situation if the membrane 41 for liquid separation is blocked, but it helps if there are problems with the sample line 60. The disadvantage would be that every additional connection, a step like change or a dead volume along the sample gas flow bath, the connection between the cavity 44 and the tube cavity 61, generate turbulences and mixes the gas columns having different gas concentrations, thus degrading the rise time of the measurement.

FIGS. 3 and 4 show from different directions cross-sectional schematic views of the airway adapter, when the liquid separator 40 is connected to the airway adapter. Both the airway adapter and the liquid separator were described in connection with FIG. 2. In FIG. 3 there is shown a central part 70 of the channel 36 extending perpendicular to a longitudinal axis of the channel towards the wall 37 of the channel. The membrane may branch from this central part 70 into at least two different branches 71, each of the at least two branches extending to different directions towards the wall 37 to obtain the sample from the breathing gas. The branches typically extend crosswise in respect to the longitudinal axis of the channel. In this specific embodiment shown in FIGS. 3 and 4 the branches 71 extend across the channel between the opposite parts of wall 37. An angle between these branches of FIGS. 3 and 4 is substantially 180 degrees, but the angle can vary and may be less than 180 degrees. Advantageously the angle may depend on the number of branches extending from the central part of the channel. The angle between different branches may be between 5-degrees depending on the number of branches, but technically it may be difficult to manufacture. More specifically the angle between different branches may be more than 90 degrees, but not more than 180 degrees to improve manufacturing and decrease the gas flow resistance and turbulences. Advantageously the angle is same between various branches extending from the central part 70 of the channel.

The opening 46 of the cavity 44, when the liquid separator 40 is connected to the airway adapter, may locate inside the channel at a predetermined distance from the wall 37. The predetermined distance from the wall may be at least 10% of a diameter of the channel 36, more specifically at least 30% of the diameter of the channel 36, or even more specifically at least 40% of the diameter of the channel 36. The most advantageous place would be in the middle of the channel 36. The opening 46 of the cavity is typically in flow communication with the at least two branches.

At least one branch may extend towards the wall and reaching the wall, but advantageously the outer surface 51 of the at least one branch may stay at a predetermined distance from the wall. The predetermined distance may be at least 2% of the diameter of the channel 36, more specifically at least 5% of the diameter of the channel 36, or even more specifically at least 10% of the diameter of the channel 36.

The central part 70 of the channel covers a middle of the channel 36, but may also cover a central area around the middle of the channel. The central area may extend around the middle of the channel towards the wall less than 25% of the diameter of the channel, more specifically less than 15% of the diameter of the channel, or even more specifically less than 5% of the diameter of the channel.

A width (W) of the branch 71 along a longitudinal axis of the channel 36 may be at least as long as the diameter of the opening 46, but typically it is at least 2 times the diameter of the opening 46, more specifically at least 4 times the diameter of the opening 46, or even more specifically at least 5 times the diameter of the opening 46. The thickness of the branch may be at least as long as the diameter of the opening 46. Typically it may be less than 6 times the diameter of the opening 46, more specifically less than 4 times the diameter of the opening 46, or even more specifically less than 2 times the diameter of the opening 46. The thickness includes a distance between the opposite outer surfaces 51 of the membrane 41 leaving therebetween the chamber 50.

Figure 5:
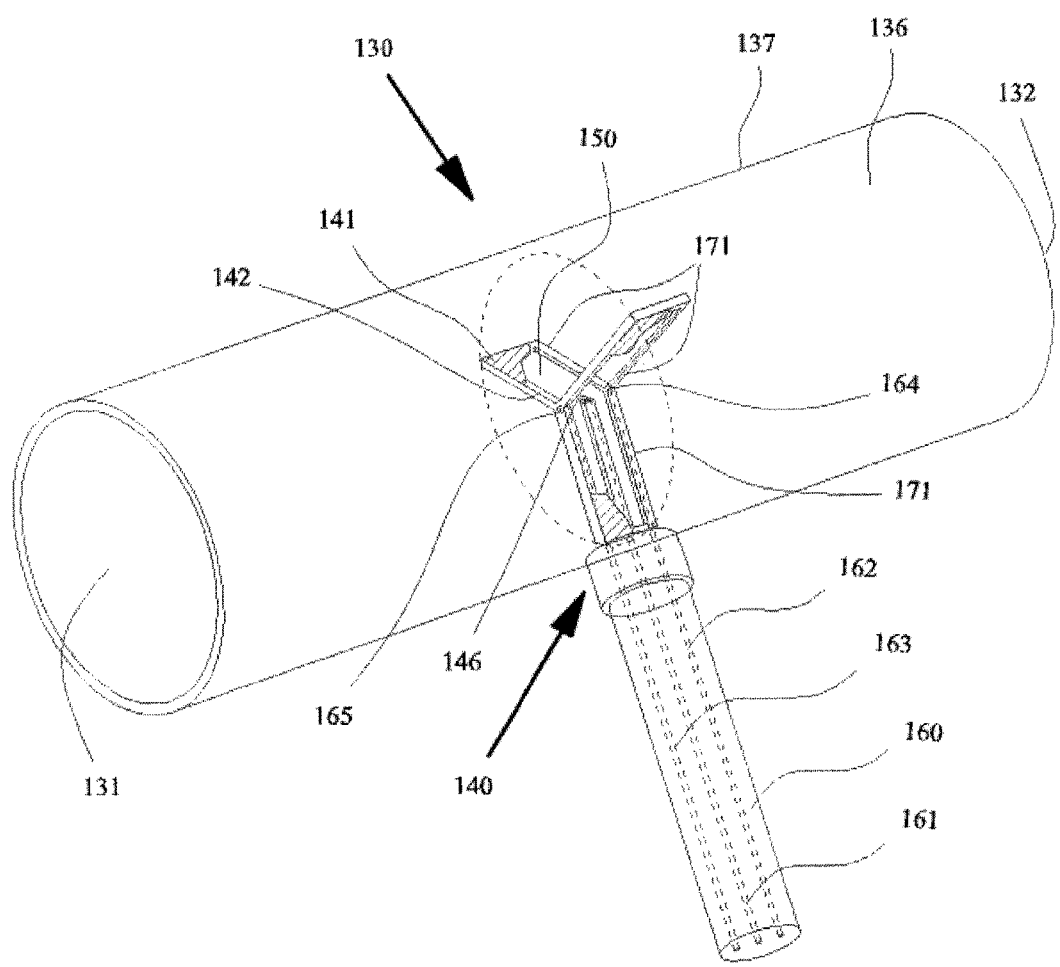
FIG. 5 shows a perspective cross-sectional view of an airway adapter with a liquid separator in accordance with another embodiment.

A perspective cross-sectional view of the airway adapter 130 with the liquid separator 140 according to another embodiment is shown in FIG. 5. The liquid separator in the airway adapter 130 differs from the one shown in FIGS. 2-4, but the liquid separation may be made following same principles as explained in connection with FIG. 2. Also in this case the liquid separator may be integrated with the airway adapter 130 or may be detachable. The rectangular supporting structure 42 with the membrane 41 has been replaced by differently shaped supporting structure 142, such as a star-shaped supporting structure, comprising the membrane 141 attached to both sides of each of the three branches 171 of the star-shape structure in liquid separator 140. One of the branches 171 in connection with the tube cavity 161 inside the sample tube 160 comprises opening 146, which opens into the middle of the star-shaped chamber 150 divided into sections, which are defined by the star-shaped supporting structure 142 and the membrane 141. The tube cavity 161 inside the sample tube 160 further connects to a sample gas pump (not shown in Figures), which sucks sample gas through the tube cavity 161, the opening 146 and the membrane 141 from the channel 136 inside the airway adapter 130 into the gas analyzer 39. The volume of the chamber 150 should be minimized, whereas the surface area of the membrane 141 is maximized as described and shown in the embodiment of FIG. 2. The star-shaped liquid separator inside the channel 136 of airway adapter 130 is position insensitive and insensible to condensate water or other liquid substances accumulating on the bottom of the channel 136 surrounded by the wall 137 since at least two of the branches 171 are always independent.

The star-shaped liquid separator 140 inside the channel 136 of the airway adapter 130 increases the flow resistance of the breathing gas flow between the first port 131 and the second port 132, but this turns into an advantage when it is combined with a breathing gas flow measurement based on pressure difference over the flow barrier, which is in this case the star-shaped construction. Thus one of the branches 171 comprises at least two pressure cavities 162 and 163 inside the sample tube 160 in connection with pressure openings 164 and 165 respectively, which further connect to pressure sensors (not shown in figure) to measure the pressure and/or the pressure difference over the flow resistance, which is in this case the star-shaped construction inside the channel 136. In FIG. 3 the cavities 161, 162 and 163 are located inside one branch 171 and one sample tube 160, which tube cavity 161 further connects to the sample gas pump and which pressure cavities 162, 163 further connects to the pressure sensors respectively located further away (not shown in Figures), but advantageously inside the gas analyzer. However it is clear that the cavities 161, 162 and 163 can be located inside the different branches 171 and the separate sample tubes if desired.

The advantage of the embodiments shown in FIGS. 2-4 and 5 is that the liquid substances are separated from the breathing gas as close to the patient as possible inside the airway adapter 30 where the liquid substances are built up and the pure gas sample continues through the sample tube 60, 160 towards the gas analyzer 45. The diameter of the cavity 44, and the tube cavity 61, 161 of the sample tube 60, 160 as well as all the cavities inside the gas analyzer (not shown in Figures) can be reduced considerably to increase the gas analyzer performance since the liquid substances cannot block the tiny cavity as they are separated already at their origin. The reduction of diameters of cavities between the liquid separator 40, 140 and the gas analyzer 45 shortens the response time, the time delay between the gas sample is taken from the breathing gas and it is analyzed since the flow speed of sample gas becomes higher in the sample tube 60, 160 and all the cavities in connection with it. Also the rise time is shortened and the capnogram accuracy increased as the mixing between different gas concentration columns and the diffusion is decreased. It is also possible to reduce the sample gas flow, but to maintain the measurement performance, which is advantageous especially with smaller children with very low tidal volumes and high respiration rates.

The written description uses examples to disclose the invention, including the best mode, and also to enable any person skilled in the art to make and use the invention. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

We claim:

1. A liquid separator for removing a liquid from a sample of a breathing gas flowing through an airway adapter having a channel surrounded by a wall, said channel being configured to locate between a patient and a ventilator, said liquid separator comprising:
    a chamber configured to receive the gas sample of the breathing gas;
    a membrane having an outer surface exposed to the breathing gas flow, said membrane at least partially surrounding the interior of said chamber and said membrane is configured to separate the liquid from the gas sample received by said chamber;
    a supporting structure for supporting said membrane; and
    a connector operationally attached to said supporting structure and which connector is connectable to said airway adapter, said connector comprising a cavity providing a flow path for the sample gas from said chamber through an opening of said cavity to a sample tube,
    wherein said membrane is configured to branch from a central part of said channel into at least two different branches, each of said at least two branches extending to different directions to obtain the sample, and
    wherein said opening is positioned in said central part of said channel.

2. The liquid separator according to claim 1, wherein each of said at least two branches are configured to extend towards said wall.

3. The liquid separator according to claim 1, wherein said opening of said cavity is configured to locate inside said channel at a predetermined distance from said wall.

4. The liquid separator according to claim 3, wherein said predetermined distance from said wall is at least 10% of a diameter of said channel.

5. The liquid separator according to claim 1, wherein said liquid separator is one of integrated with said airway adapter and detachably connected to said airway adapter.

6. The liquid separator according to claim 1, wherein said at least two branches with said membrane are configured to extend crosswise in respect to a longitudinal axis of said channel from a central part of said channel.

7. The liquid separator according to claim 1, wherein said membrane is configured to branch from a central part of said channel into at least three different branches, each branch into different directions towards the wall.

8. The liquid separator according to claim 2, wherein said at least two different branches towards the wall are configured to form an angle which is one of equal to 180 degrees and less than 180 degrees.

9. The liquid separator according to claim 8, wherein said angle which is less than 180 degrees is between 5-90 degrees.

10. The liquid separator according to claim 1, wherein said branches at least partially restrict the breathing gas flow through said channel diverting a portion of the breathing gas flow to the sample tube, providing an indication of the breathing gas flow.

11. The liquid separator according to claim 2, wherein said membrane of at least one branch of said at least two branches is configured to reach said wall or is configured to stay at a predetermined distance from said wall.

12. The liquid separator according to claim 11, wherein said predetermined distance from said wall is at least 2% of a diameter of said channel.

13. The liquid separator according to claim 1, wherein said central part of the channel is configured to cover a central area around the middle of said channel.

14. The liquid separator according to claim 1, wherein said central part is configured to extend around the middle of said channel towards said wall less than 25% of a predetermined diameter of said channel.

15. An airway adapter comprising:
    a channel surrounded by a wall for a breathing gas flow, said channel being configured to locate between a patient and a ventilator;
    a first port for delivering breathing gas;
    a second port for delivering breathing gas, said second port being in flow communication with said first port through said channel; and
    a liquid separator extending into said channel for removing a liquid from a sample of the breathing gas flowing through said channel, said liquid separator comprising a chamber configured to receive the sample of the breathing gas, a membrane having an outer surface exposed to the breathing gas flow, said membrane at least partially surrounding the interior of said chamber and said membrane is configured to separate the liquid from the gas sample configured to be received by said chamber, a supporting structure for supporting said membrane, and a connector operationally attached to said supporting structure, said connector comprising a cavity providing a flow path for the sample gas from said chamber through an opening of said cavity to a sample tube, said connector being operationally connected to said wall, wherein said membrane is configured to branch from a central part of said channel into at least two different branches, each of said at least two branches extending to different directions towards said wall to obtain the sample, and wherein said opening is positioned in said central port of said channel.

16. The airway adapter according to claim 15, further comprising a third port in said wall, said connector of said liquid separator being one of integrated with said third port of said wall and detachably connected to said third port.

17. The airway adapter according to claim 16, wherein said third port is covered by a penetrable membrane through which said liquid separator is configured to be moved into the said channel.

18. The airway adapter according to claim 15, wherein said at least two branches with said membrane are configured to extend crosswise in respect to a longitudinal axis of said channel from a central part of said channel.

19. The airway adapter according to claim 15, wherein at least one branch of said at least two branches is configured to stay at a predetermined distance from said wall, said predetermined distance from said wall being at least 2% of a diameter of said channel.

20. An airway adapter comprising:
a channel surrounded by a wall for a breathing gas flow, said channel being configured to locate between a patient and a ventilator;
a first port for delivering breathing gas;
a second port for delivering breathing gas, said second port being in flow communication with said first port through said channel; and
a liquid separator extending into said channel for removing a liquid from a sample of the breathing gas flowing through said channel, said liquid separator comprising a chamber configured to receive the sample of the breathing gas, a membrane having an outer surface exposed to the breathing gas flow, said membrane at least partially surrounding the interior of said chamber and said membrane is configured to separate the liquid from the gas sample configured to be received by said chamber, a supporting structure for supporting said membrane, and a connector operationally attached to said supporting structure, said connector comprising a cavity providing a flow path for the sample gas from said chamber through an opening of said cavity to a sample tube, said connector being operationally connected to said wall,
wherein said membrane is configured to branch from a central part of said channel into at least two different branches, each of said at least two branches extending to different directions towards said wall to obtain the sample, and that said branches at least partially restrict the breathing gas flow through said channel, diverting a portion of the breathing gas flow to the sample tube, providing an indication of the breathing gas flow, and
wherein said opening is positioned in said central part of said channel.

* * * * *